US011274059B2

(12) United States Patent
Deng et al.

(10) Patent No.: US 11,274,059 B2
(45) Date of Patent: Mar. 15, 2022

(54) BIOACTIVE GLASS COMPOSITIONS AND DENTIN HYPERSENSITIVITY REMEDIATION

(71) Applicant: CORNING INCORPORATED, Corning, NY (US)

(72) Inventors: Huayun Deng, Painted Post, NY (US); Ye Fang, Painted Post, NY (US); Qiang Fu, Painted Post, NY (US); John Christopher Mauro, Boalsburg, PA (US); Michael S Pambianchi, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 16/203,002

(22) Filed: Nov. 28, 2018

(65) Prior Publication Data

US 2019/0161393 A1    May 30, 2019

Related U.S. Application Data

(60) Provisional application No. 62/591,423, filed on Nov. 28, 2017.

(51) Int. Cl.
| | |
|---|---|
| *A61K 6/00* | (2020.01) |
| *A61K 33/06* | (2006.01) |
| *A61K 8/25* | (2006.01) |
| *A61K 31/69* | (2006.01) |
| *C03C 3/19* | (2006.01) |
| *C03C 3/064* | (2006.01) |
| *C03C 3/087* | (2006.01) |
| *C03C 3/091* | (2006.01) |
| *C03C 3/097* | (2006.01) |
| *A61Q 11/00* | (2006.01) |
| *C03C 4/00* | (2006.01) |
| *A61K 8/21* | (2006.01) |
| *A61K 8/19* | (2006.01) |
| *A61K 8/26* | (2006.01) |
| *A61K 6/20* | (2020.01) |
| *A61K 6/77* | (2020.01) |
| *A61K 6/836* | (2020.01) |

(52) U.S. Cl.
CPC .............. *C03C 4/0021* (2013.01); *A61K 6/20* (2020.01); *A61K 6/77* (2020.01); *A61K 6/836* (2020.01); *A61K 8/19* (2013.01); *A61K 8/21* (2013.01); *A61K 8/25* (2013.01); *A61K 8/26* (2013.01); *A61Q 11/00* (2013.01); *C03C 3/064* (2013.01); *C03C 3/097* (2013.01)

(58) Field of Classification Search
CPC ........ A61K 6/833; A61K 6/836; A61K 33/08; A61K 33/22; A61K 8/25; A61K 8/26; A61K 6/77; A61K 8/24; A61K 2300/00; A61K 33/42; A61K 6/30; A61K 6/20; A61K 6/54; A61Q 11/00; C03C 4/0021; C03C 2205/06; C03C 3/097; C03C 3/091; C03C 4/0007; C03C 3/062; C03C 3/087; C03C 2204/02; C03C 12/00; C03C 3/064; C03C 2204/00; C03C 3/083; C03C 3/089; C03C 3/14; A01N 59/06; A01N 59/14; A01N 59/26

See application file for complete search history.

(56) References Cited

U.S. PATENT DOCUMENTS

| | | |
|---|---|---|
| 2,532,386 A | 12/1950 | Armistead |
| 2,978,339 A | 4/1961 | Franklin et al. |
| 2,987,339 A | 4/1961 | Veatch et al. |
| 3,323,888 A | 6/1967 | Searight et al. |
| 3,778,335 A | 12/1973 | Boyd |
| 3,790,430 A | 2/1974 | Mochel |
| 4,083,727 A | 4/1978 | Andrus et al. |
| 4,084,972 A | 4/1978 | Andrus et al. |
| 4,126,437 A | 11/1978 | O'Horo |
| 4,140,645 A | 2/1979 | Beall et al. |
| 4,233,169 A | 11/1980 | Beall et al. |
| 4,323,056 A | 4/1982 | Borrelli et al. |
| 4,340,693 A | 7/1982 | Drake et al. |
| 4,391,646 A | 7/1983 | Howell |
| 4,889,707 A | 12/1989 | Day et al. |
| 5,024,973 A | 6/1991 | Kondo et al. |
| 5,081,394 A | 1/1992 | Morishita et al. |
| 5,153,070 A | 10/1992 | Andrus et al. |
| 5,217,928 A | 6/1993 | Goetz et al. |
| 5,648,124 A | 7/1997 | Sutor |
| 5,674,790 A | 10/1997 | Araujo |
| 5,849,816 A | 12/1998 | Suskind et al. |
| 5,876,452 A | 3/1999 | Athanasiou et al. |
| 6,034,014 A | 3/2000 | Rapp et al. |
| 6,214,471 B1 | 4/2001 | Beall et al. |
| 6,254,981 B1 | 7/2001 | Castle |
| 6,280,863 B1 | 8/2001 | Frank et al. |
| 6,328,990 B1 | 12/2001 | Ducheyne et al. |

(Continued)

FOREIGN PATENT DOCUMENTS

| | | |
|---|---|---|
| CA | 2577628 C | 3/2006 |
| CA | 2926665 A1 | 5/2015 |
| CN | 1054055 A | 8/1991 |
| CN | 1155844 A | 7/1997 |
| CN | 1838936 A | 9/2006 |

(Continued)

OTHER PUBLICATIONS

Abo-Naf et al; "In Vitro Bioactivity Evaluation, Mechanical Properties and Microstructural Characterization of Na2O—CaO—B2O3—P2O5 Glasses"; Spectrochimica Acta Part A: Molecular and Biomolecular Spectroscopy; 144 (2015) pp. 88-98.

(Continued)

*Primary Examiner* — Tracy Liu (57) ABSTRACT

A dental formulation including: a bioactive glass composition as defined herein, in an effective amount; and a suitable carrier as defined herein, in an effective amount. Also disclosed is a method of making and using the dental formulation to treat, for example, dentin sensitivities.

11 Claims, 4 Drawing Sheets

(56) References Cited

U.S. PATENT DOCUMENTS

| | | | |
|---|---|---|---|
| 6,338,751 B1 | 1/2002 | Litkowski et al. |
| 6,506,399 B2 | 1/2003 | Donovan |
| 6,514,892 B1 | 2/2003 | Kasai et al. |
| 6,802,894 B2 | 10/2004 | Brodkin et al. |
| 6,838,171 B2 | 1/2005 | Normura |
| 6,852,656 B1 | 2/2005 | La Greca et al. |
| 7,047,637 B2 | 5/2006 | Derochemont et al. |
| 7,166,548 B2 | 1/2007 | Apel et al. |
| 7,166,549 B2 | 1/2007 | Fechner |
| 7,192,602 B2 | 3/2007 | Fechner et al. |
| 7,316,740 B2 | 1/2008 | Schweiger et al. |
| 7,597,900 B2 | 10/2009 | Zimmer et al. |
| 7,704,903 B2 | 4/2010 | Seneschal et al. |
| 7,709,027 B2 | 5/2010 | Fechner et al. |
| 7,905,115 B2 | 3/2011 | Rake et al. |
| 7,989,065 B2 | 8/2011 | Winstead et al. |
| 8,080,490 B2 | 12/2011 | Fechner et al. |
| 8,173,154 B2 | 5/2012 | Jung et al. |
| 8,637,300 B2 | 1/2014 | Ruf et al. |
| 9,056,045 B2 | 6/2015 | Hughes |
| 9,084,844 B2 | 7/2015 | Vallittu |
| 9,101,439 B2 | 8/2015 | Ritzberger et al. |
| 9,168,272 B2 | 10/2015 | Hill et al. |
| 9,232,989 B2 | 1/2016 | Ritzberger et al. |
| 9,241,879 B2 | 1/2016 | Castillo |
| 9,326,995 B2 | 5/2016 | Stucky et al. |
| 9,498,459 B2 | 11/2016 | Pomrink et al. |
| 9,622,483 B2 | 4/2017 | Bookbinder et al. |
| 9,688,567 B2 | 6/2017 | Rampf et al. |
| 9,701,573 B2 | 7/2017 | Beall et al. |
| 2004/0120908 A1 | 6/2004 | Cohen et al. |
| 2004/0228905 A1 | 11/2004 | Greenspan et al. |
| 2005/0118236 A1 | 6/2005 | Qiu et al. |
| 2005/0142077 A1* | 6/2005 | Zimmer ............... C03C 4/0007 424/57 |
| 2005/0158395 A1 | 7/2005 | Zimmermann et al. |
| 2006/0127427 A1 | 6/2006 | Vernice et al. |
| 2006/0292280 A1 | 12/2006 | Soper et al. |
| 2007/0122356 A1* | 5/2007 | Kessler ............... A61K 6/0017 424/49 |
| 2007/0281033 A1 | 12/2007 | Rochat |
| 2008/0214428 A1 | 9/2008 | Orlich et al. |
| 2008/0233201 A1 | 9/2008 | Royere et al. |
| 2009/0208428 A1 | 8/2009 | Hill et al. |
| 2009/0324668 A1 | 12/2009 | Kangasniemi et al. |
| 2011/0008293 A1 | 1/2011 | Bhandari |
| 2011/0009254 A1 | 1/2011 | Schweiger et al. |
| 2011/0152057 A1 | 6/2011 | Qi |
| 2012/0020898 A1* | 1/2012 | Mandadi ............... A61K 8/25 424/52 |
| 2012/0135848 A1 | 5/2012 | Beall et al. |
| 2012/0317735 A1 | 12/2012 | Gonzales et al. |
| 2012/0321567 A1 | 12/2012 | Gonzales et al. |
| 2013/0011446 A1 | 1/2013 | DePaula |
| 2013/0266625 A1 | 10/2013 | Benita et al. |
| 2014/0000891 A1 | 1/2014 | Mahoney et al. |
| 2014/0026916 A1 | 1/2014 | Havens et al. |
| 2014/0186274 A1 | 7/2014 | Hodgkinson |
| 2014/0193499 A1 | 7/2014 | Da Fonte Ferreira et al. |
| 2014/0212469 A1 | 7/2014 | Rahaman et al. |
| 2014/0219941 A1 | 8/2014 | Takekawa et al. |
| 2014/0271913 A1 | 9/2014 | Pomrink et al. |
| 2014/0349831 A1 | 11/2014 | Cornejo et al. |
| 2014/0370464 A1 | 12/2014 | Kounga et al. |
| 2015/0087493 A1 | 3/2015 | Ritzberger et al. |
| 2015/0104655 A1 | 4/2015 | Kim et al. |
| 2015/0231042 A1 | 8/2015 | Gonzales et al. |
| 2015/0239772 A1 | 8/2015 | Baker et al. |
| 2015/0265509 A1 | 9/2015 | Zhang et al. |
| 2015/0299031 A1 | 10/2015 | Ritzberger et al. |
| 2015/0374589 A1 | 12/2015 | Rempf et al. |
| 2016/0060159 A1 | 3/2016 | Kim et al. |
| 2016/0102010 A1 | 4/2016 | Beall et al. |
| 2016/0145567 A1 | 5/2016 | Henry et al. |
| 2016/0340239 A1 | 11/2016 | Propster et al. |
| 2017/0086877 A1 | 3/2017 | Moffarah et al. |
| 2017/0274118 A1 | 9/2017 | Nazhat et al. |
| 2017/0340527 A1 | 11/2017 | Chang et al. |
| 2017/0340666 A1 | 11/2017 | Deng et al. |
| 2017/0341975 A1 | 11/2017 | Gross et al. |
| 2017/0342382 A1 | 11/2017 | Deng et al. |
| 2017/0342383 A1 | 11/2017 | Deng et al. |
| 2017/0349876 A1 | 12/2017 | Deng et al. |
| 2017/0354755 A1 | 12/2017 | Weinberger et al. |
| 2018/0343255 A1 | 11/2018 | Thibadeau, Sr. et al. |
| 2019/0060523 A1 | 2/2019 | Bakry |

FOREIGN PATENT DOCUMENTS

| | | |
|---|---|---|
| CN | 101018573 A | 8/2007 |
| CN | 101407373 A | 4/2009 |
| CN | 101500622 A | 8/2009 |
| CN | 101596326 A | 12/2009 |
| CN | 101704632 A | 5/2010 |
| CN | 102421716 A | 4/2012 |
| CN | 102430149 A | 5/2012 |
| CN | 102526797 A | 7/2012 |
| CN | 103172263 A | 6/2013 |
| CN | 103979796 A | 8/2014 |
| CN | 104108883 A | 10/2014 |
| CN | 104379113 A | 2/2015 |
| CN | 104876439 A | 9/2015 |
| CN | 105236745 A | 1/2016 |
| CN | 105819697 A | 8/2016 |
| EP | 0583791 A1 | 2/1994 |
| EP | 1123072 A1 | 8/2001 |
| EP | 1452496 A1 | 9/2004 |
| EP | 1021148 B1 | 5/2008 |
| HU | 227595 B1 | 9/2011 |
| JP | 2001-010843 A | 1/2001 |
| JP | 2004359754 A | 12/2004 |
| JP | 2005-053776 A | 3/2005 |
| JP | 2007001846 A | 1/2007 |
| JP | 2007039269 A | 2/2007 |
| JP | 2015-504399 A | 2/2015 |
| JP | 2015-505786 A | 2/2015 |
| JP | 2015-509016 A | 3/2015 |
| JP | 2015-525180 A | 9/2015 |
| KR | 2007081952 A | 8/2007 |
| KR | 10-0781671 B1 | 12/2007 |
| KR | 20130112433 A | 10/2013 |
| WO | 87/07256 A1 | 12/1987 |
| WO | 1991012032 A1 | 8/1991 |
| WO | 1997018171 A1 | 5/1997 |
| WO | 9727148 A1 | 7/1997 |
| WO | 1998015263 A2 | 4/1998 |
| WO | 199962835 A1 | 12/1999 |
| WO | 00/15167 A1 | 3/2000 |
| WO | 01/34060 A1 | 5/2001 |
| WO | 2007/022264 A2 | 2/2007 |
| WO | 2007141978 A1 | 12/2007 |
| WO | 2008000888 A2 | 1/2008 |
| WO | 2011/084572 A2 | 7/2011 |
| WO | 2011141896 A1 | 11/2011 |
| WO | 2012/091201 A1 | 7/2012 |
| WO | 2014015240 A1 | 1/2014 |
| WO | 2014095198 A1 | 6/2014 |
| WO | 2014159240 A1 | 10/2014 |
| WO | 2015034860 A1 | 3/2015 |
| WO | 2015123049 A1 | 8/2015 |
| WO | 2015200017 A1 | 12/2015 |

OTHER PUBLICATIONS

Sharmikn et al; "Effect of Boron Additiona on The Thermal, Degradation, and Cytocompatibility Properties of Phosphate-Baed Glasses"; Biomed Research International; vol. 2013; Article ID 902472; 12 Pages.

Buchilin et al; "Crystallization-Controlled Pore Retention in Calcium-Phosphate Glassceramics from Powder Sintering of CaO—P2O5—B2O3—Al2O3—TiO2—ZrO2 Glass"; Journal of Non-Crystalline Solids; 373-374 (2013) pp. 42-50.

(56) References Cited

OTHER PUBLICATIONS

Zheng et al; "Characteristics and Biocompatibility of Na2O—K2O—CaO—MgO—SrO—B2O3—P2O5 Borophosphate Glass Fibers"; Journal of Non-Crystalline Solids; 358 (2012) 387-391.

"Azo Materials, ""Silicon Dioxide"", accessed from: ""https://www.azom.com/properties.aspx?ArticleI D=1114"", accessed on Feb. 19, 2019,pp. 1-4 (Year: 2019)".

Kaklamani et al; "Mechanical Properties of Alginate Hydrogels Manufactured Using External Gelation", J. MeECH Beh. Biomed. Mater., 2014, pp. 135-142 (Year: 2014).

Maestrelli et al; "Development of Enteric-Coated Calcium Pectinate Microspheres Intended for Colonic Drug Delivery", Eur. J. Pharm. And Biopharm., 2008, pp. 508-518 (Year: 2008).

Mohini et al; "Studies on Influence of Aluminium Ions on The Bioactivity of B2O3—SiO2—P2O5—Na2O—CaO Glass System by Means of Spectroscopic Studies"; Applied Surface Science; 287 (2013) p. 46-53.

Noris-Suarez et al; "Osteoblastic Cells Biomineralized on Bioactive Glass and Glass-Ceramics of The SiO2Na20.CaO.K2O.MgO.P2O5 System Modified With Al2O3 and B2O3"; Journal of Ceramic Processing Research; vol. 11, No. 2 (2010) p. 129-137.

Pires et al; "The Role of Alumina in Aluminoborosilicate Glasses for Use in Glass-Ionomer Cements"; J. Mater. Chem, 19 (2009) p. 3652-3660.

Invitation to Pay Additional Fees From The International Searching Authority; PCT/US2018/062671; dated Mar. 7, 2019; 11 Pages; European Patent Office.

Ahmed et al; "Processing, Characterisation and Biocompatibility of Iron-Phosphate Glass Fibres for Tissue Engineering", Biomaterials, 25, (2004), 3223-3232.

American Type Culture Collection, Product Sheet MC3T3E1, Subclone 14(ATCC® CRL2594 ™), p. 1-3, Aug. 2014.

Apel et al., "Influence of ZrO2 on The Crystallization and Properties of Lithium Disilicate Glass-Ceramics Derived From a Multi-Component System", J Eur Ceram Soc, 2007, 27:1571-1577.

Bertling, et al., "Hollow Microspheres". Chem Eng Technol, 2004, 27: 829-837.

Brown et al; "Effect of Borate Glass Composition on Its Conversion to Hydroxyapatite and on The Proliferation of MC3T3-E1 Cells"; Journal of Biomedical Materials Research Part A 88, No. 2, (2009): 392-400.

Budov, "Hollow Glass Microspheres. Use, Properties and Technology (Review Article)", Glass Ceram, 1994, 51: 230-235.

Bunker, et al., "Phosphate Glass Dissolution in Aqueous Solutions", Journal of Noncrystalline Solids 64 (1984) 291-316.

Cao et al; "Bioactive Materials"; Ceramics International, 22, (1996) 493-507.

Cao et al; "Methods for Biomimetic Remineralization of Human Dentine: A Systematic Review", Int. J. Mol. Sci. (2015) 16; pp. 4615-4627.

Copeland et al; "Microbeads: An Emerging Water Quality Issue", Retrieved From fas.org, Jul. 20, 2015, 2 pgs.

Coradin et al; "Silica-Alginate Composites for Microencapsulation" Applied Microbiology and Biotechnology, 61(5-6) pp. 429-434 (2003).

Davari, "Dentin Hypersensitivity: Etiology, Diagnosis and Treatment, A Literature Review," J Dent (Shiraz), 2013, 14(3): 136-145).

De Kerchove et al., "Formation of Polysaccharide Gel Layers in The Presence of Ca2+ and K + Ions: Measurements and Mechanisms", Biomacromolecules 2007, 8, 113-121.

El-Kheshen et al; "Effect of Al2O3 Addition on Bioactivity, Thermal and Mechanical Properties of Some Bioactive Glasses"; Ceramics Int. (2008) 34: 1667-1673 (Year: 2008).

Fendall et al; "Contributing to Marine Pollution by Washing Your Face: Microplasitcs in Facial Cleansers"; Marine Pollution Bulletin 58 (8):1225-1228 (2009)).

Forsback et al; "Mineralization of Dentin Induced by Treatment With Bioactive Glass S53P4 In Vitro"; Acta Odontol Scand, 62 (2004); pp. 14-20.

Franks et al; "The Effect of MgO on The Solubility Behaviour and Cell Proliferation in a Quaternary Soluble Phosphate Based Glass System", J. of Mate. Science: Materials in Medicine, 13, (2002), 549-556.

Fu et al; "Bioactive Glass Innovations Through Academia-Industry Collaboration"; International Journal of Applied Glass Science, 7 [2], (2016) p. 139-146.

Fu et al; "Bioactive Glass Scaffolds for Bone Tissue Engineering: State of The Art and Future Perspectives", Materials Science and Engineering, C 31, (2011), 1245-1256.

Fu et al; "Hollow Hydroxyapatite Microspheres As a Device for Controlled Delivery of Proteins"; J Mater Sci: Mater Med., 2011;22:579-91.

Fu et al; "Nature-Inspired Design of Strong, Tough Glass-Ceramics," MRS Bulletin, 2017, 42:220-225.

Fu et al; "Silicate, Borosilicate, and Borate Bioactive Glass Scaffolds With Controllable Degradation Rate for Bone Tissue Engineering Application. I. Preparation and In Vitro Degradation"; J. Biomed. Res. (2010) 95A(1): 164-171(Year:2010).

Graham, "High-Sensitivity Manetization Measurements", J. Mater. Sci. Technol., vol. 16, No. 2, 2000, p. 97-101.

Gy, "Ion Exchange for Glass Strengthening," Mater Sci EHG B, 2008, 149: 159-165.

Han et al; "In Vivo Remineralization of Dentin Using an Agarose Hydrogel Biomimetic Mineralization System"; Nature, Scientific Reports; (2017); 9 Pages.

Hench et al; "Third-Generation Biomedical Materials", Science, vol. 295, Feb. 8, 2002, p. 1016-1017, www.sciencemag.org, Downloaded From www.sciencemag.org on Aug. 5, 2015.

Hench; "Bioceramics", J. Am. Ceram. Soc., 81, (7), 1705-1728 (1998).

Hiorth et al; "Immersion Coating of Pellets With Calcium Pectinate and Chitosan"; International Journal of Pharmaceutics 308 (2006) 25-32.

Holand et al; "A Comparison of the Microstructure and Properties of The IPS EMPRESST2 and The IPS EMPRESST Glass-Ceramics"; J Biomed Mater Res (Appl Biomater), 2000, 53: 297-303.

Huang et al; "Kinetics and Mechanisms of The Conversion of Silicate (45S5), Borate and Borosilicate Glasses to Hydroxyapatite in Dilute Phosphate Solutions," J Mater Sci Mater Med 2006, 17: 583-596.

Jacoby; "New Applications for Glass Emerge," Chem. Eng. News, 90 [25] 34-36 (2012).

Jones; "Review of Bioactive Glass: From Hench to Hybrids"; Acta Biomaterialia 9 (2013) pp. 4457-4486.

Knowles; "Phosphate Based Glasses for Biomedical Applications"; J Mater. Chem. 2003, 13, 2395-2401.

Kokubo et al; "How Useful is SBF in Predicting In Vivo Bone Bioactivity?"; Biomaterials, 27, (2006), 2907-2915.

Kulal et al; "An In-Vitro Comparison of Nano Hydroxyapatite, Novamin and Proargin Desensitizing Toothpastes—A SEM Study"; Journal of Clinical and Diagnostic Research; 2016; vol. 10 (10) ZC51-ZC54.

Kumaryadav et al; "Development of Zirconia Substituted 1393 Bioactive Glass for Orthopaedic Application"; Oriental Journal of Chemistry; vol. 33, No. 6; (2017) pp. 2720-2730.

Lien et al; "Microstructural Evolution and Physical Behavior of a Lithium Disilicate Glass-Ceramic"; Dent Mater 2015, 31: 928-940.

Low et al; "Reduction in Dental Hypersensitivity With Nano-Hydroxyapatite, Potassium Nitrate, Sodium Monoflurophosphate and Antioxidants"; The Open Dentistry Journal; (2015), 9, pp. 92-97.

Lu et al; "The Biodegradation Mechanism of Calcium Phosphate Biomaterials in Bone"; Journal of Biomedical Materials Research, Aug. 2002, 63(4): 408-412.

Marcolongo et al; "Surface Reaction Layer Formation In Vitro on a Bioactive Glass Fiber/Polymeric Composite"; J. Biomed Mater. Res.; (1997); 37, p. 440-448.

Miglani et al; "Dentin Hypersensitivity: Recent Trends in Management"; J. Conserv. Dent. 2010; 13 (4) pp. 218-224.

Mintatoya et al; "Bioactive Glass Cloth That Propmotes New Bone Formation"; Key Eng. Mater.; (2013) 529-530; pp. 266-269.

(56) References Cited

OTHER PUBLICATIONS

Montazerian et al; "History and Trends of Bioactive Glass-Ceramics", Journal of Biomedical Materials Research A, 2016, vol. 104A, 1231-1249, 2016 Wiley Periodicals, Inc.
Morch et al; "Effect of Ca2+, Ba2+, and Sr2+ on Alginate Microbeads"; Biomacromolecules 2006, 7, 1471-1480.
Murray; "Issues in Boron Risk Assessment: Pivotal Study, Uncertainty Factors, and ADIs"; The Journal of Trace Elements in Experimental Medicine 9, No. 4 (1996): 231-243.
Napper et al; "Characterisation, Quantity and Sorptive Properites of Microplastics Extracted From Cosmetics"; Marine Pollution Bulletin, vol. 99, Issues 1-2, Oct. 15, 2015, p. 178-185.
Neel et al; "Effect of Iron on The Surface, Degradation and Ion Release Properties of Phosphate Based Glass Fibres." Acta Biomaterialia 1, No. 5 (2005): 553-563.
Neel, et al; "Characterisation of Antibacterial Copper Releasing Degradable Phosphate Glass Fibres." Biomaterials 26, No. 15 (2005): 2247-2254.
Gorustovich et al. "Osteoconductivity of strontium-doped bioactive glass particles: A histomorphometric study in rats," J Biomed Materials Res. Part A (2010) 92A: pp. 232-237.
Harianawala et al. "Biocompatibility of Zirconia" , J Adv Med Deni Sci Res 4(3) 2016, pp. 35-39.
Ohgushi et al; Bioceramics vol. 11, Legeros et al, Ed., Proc. 11th Int. Symp. Ceramics. Med. (NY:NY), Nov. 1998, pp. 261-264 (Year 1998).
Peddi et al; "Bioactive Borate Glass Coatings for Titanium Alloys", J. Mater. Sci: Mater. Med., (2008), 19, p. 3145-3152.
Rahman et al; "Bioactive Glass in Tissue Engineering", Acta Biomaterialia, 7, (2011), 2355-2373.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.
Raszewski et al; "Methods for Producing Hollow Glass Microspheres"; Savannah River National Laboratory, Aiken SC 29808, Mar. 2016.
Rochman et al; "Scientific Evidence Supports a Ban on Microbeads", Environ Sci & Tech, 2015, 49: 10759-10761.
Saranti, et al., "Bioactive Glasses in The System CaO—B2O3—P2O5: Preparation, Structural Study and In Vitro Evaluation." Journal of Non-Crystalline Solids 352, No. 5 (2006): 390-398.
Sglavo; "Chemical Strengthening of Soda Lime Silicate Float Glass: Effect of Small Differences in The KNO3 Bath," Int J Appl Glass Sci, 2015, 6: 72-82.
Simhan; "Chemical Durability of ZrO2 Containing Glasses"; Journal of Non-Crystalline Solids; 54 (1983) 335-343.
Singh et al; "Characterization of Si02—Na20—Fe203—Ca0—P205_B203 Glass Ceramics"; Journal of Materials Science: Materials in Medicine, 10(8) pp. 481-484. (1999).
Strassler et al; "Dentinal Hypersensitivity: Etiology, Diagnosis and Management"; 9 Pages; Date Unknown; www.indeedce.com.
Succaria et al; "Prescribing A Dental Ceramic Material: Zirconia Vs Lithium-Disilicate"; The Saudi Dent J, 2011, 23: 165-166.
Tilocca et al., "Structural Effects of Phosphorus Inclusion in Bioactive Silicate Glasses", J. Phys. Chem. B 2007, 111, 14256-14264.
Topuz et al; "Magnesium Ions and Alginate do Form Hydrogels: A Rheological Study"; Soft Matter, 2012, 8, 4877-4881.
Uo et al; "Properties and Cytotoxicity of Water Soluble Na2O—CaO—P205 Glasses"; Biomaterials, 19, (1998), 2277-2284.
Wallenberger et al; "The Liquidus Temperature; Its Critical Role in Glass Manufacturing"; International Journal of Applied Glass Science 1 [2] (2010) p. 151-163.
Xiao et al; "Hollow Hydroxyapatite Microspheres: A Novel Bioactive and Osteoconductive Carrier for Controlled Release of Bone Morphogenetic Protein-2 in Bone Regeneration", Acta Biomater. Sep. 2013 ; 9(9): 8374-8383.
Yao et al; "In Vitro Bioactive Characteristics of Borate-Based Glasses With Controllable Degradation Behavior"; J. Am. Ceram. Soc.; 90 [1]; 303-306 (2007).
Yin et al; "Effect of ZrO2 on the Bioactivity Properties of Gel-Derived CaO—P2O5—SiO2—SrO Glasses"; Ceramics International; 43 (2017) p. 9691-9698.
Yuan et al; "Osteoinduction by Calciumphosphate Biomaterials", Journal of Materials Science: Materials in Medicine 9 (1998) 723-726.
Yue et al; "Fiber Spinnability of Glass Melts"; International Journal of Applied Glass Science; (2016) p. 1-11.
Zanotto, "A Bright Future for Glass-Ceramics", American Ceramic Society Bulletin, vol. 89, No. 8, pp. 19-27, 2010.
Zhang et al; "Chipping Resistance of Graded Zirconia Ceramics for Dental Crowns"; J Dent Res, 2012, 91:311-315.
Andersson et al. "In vivo behaviour of glasses in the SiO2—Na2O—CaO—P2O5—Al2O—B2O3 system", J. Mat. Sci: Materials in Medicine (1990) 1: pp. 219-227.
Ogonczyk et al. "Microfluidic formulation of pectin microbeads for encapsulation and controlled release of nanoparticles," Biomicrofluidics, 2011, pp. 1-12.
Gunter et al. "Calcium pectinate gel beads obtained from callus cultures pectins aspromising systems for colon-targeted drug delivery," Carbohydrate Polymers, 2016, pp. 490-499.
Zahid et al; "Biological Behavior of Bioactive Glasses and Their Composites" ; RSC Adv., 2016, 6 Pages 70197-70214.
Ohgushi et al., "Al2O3 doped apatite-wollastonite containing glass ceramic provokes osteogenic differentiation of marrow stromal stem cells", J Biomed Mater Re, vol. 44, Issue 4 pp. 381-388.
Zhao et al., "Mechanism for converting Al2O3-containing borate glass to hydroxyapatite in aqueous phosphate solution", Acta Biomaterialia, Dec. 10, 2006, vol. 5, No. 4, pp. 1265-1273.
Ning et al., "Food Biochemistry" South China University of Technology Press, Edition 1, 1995, 9 pages (5 pages of English Translation and 14 pages of Original Document).
Liu et al. "The Effect of Novel Fluorapatite Surfaces on Osteoblast-Like Cell Adhesion, Growth, and Mineralization" Tissue Engineering: Part A, vol. 16, No. 9, 2010 (Year: 2010).
Wang Yingjun, "Biomedical Ceramic Materials", Guangzhou, South China University of Science and Technology Press, , Aug. 31, 2010, pp. 90-93(Original document only).

* cited by examiner

BIOACTIVE GLASS COMPOSITIONS AND DENTIN HYPERSENSITIVITY REMEDIATION

CROSS-REFERENCE TO RELATED APPLICATIONS

This application claims the benefit of priority under 35 U.S.C. § 119 of U.S. Provisional Patent Application No. 62/591,423 filed Nov. 28, 2017, the content of which is incorporated herein by reference in its entirety.

The present application is related commonly owned and assigned U.S. Ser. No. Provisional Application Nos., filed May 25, 2016:

62/342,384, entitled "BIOACTIVE ALUMINOBORATE GLASSES";

62/342,377, entitled "MAGNETIZABLE GLASS CERAMIC COMPOSITION AND METHODS THEREOF";

62/342,381, entitled "LITHIUM DISILICATE GLASS-CERAMIC COMPOSITIONS AND METHODS THEREOF";

62/342,391, entitled "BIODEGRADABLE MICROBEADS"; and

62/342,411, entitled "BIOACTIVE GLASS MICROSPHERES"; but does not claim priority thereto.

The present application is also related to commonly owned and assigned U.S. Ser. No. Application No., 62/189,880, filed Jul. 7, 2015, entitled "ANTIMICROBIAL PHASE-SEPARATING GLASS AND GLASS CERAMIC ARTICLES AND LAMINATES," which mentions a copper containing laminate having a degradable phase, which phase liberates cooper ion, and a non-degradable phase, but does not claim priority thereto.

The present application is also related commonly owned and assigned U.S. Ser. No. Application Nos.:

62/591,446, filed Nov. 28, 2017, entitled "HIGH LIQUIDUS VISCOSITY BIOACTIVE GLASS"; and 62/591,438, filed Nov. 28, 2017, entitled "CHEMICALLY STRENGTHENED BIOACTIVE GLASS-CERAMICS";

62/591,429, filed Nov. 28, 2017, entitled "BIOACTIVE BORATE GLASS AND METHODS THEREOF", filed concurrently herewith, but does not claim priority thereto.

The entire disclosure of each publication or patent document mentioned herein is incorporated by reference.

BACKGROUND

The disclosure relates to a glass composition, a bioactive glass composition, and to methods of making and using the compositions.

SUMMARY

In embodiments, the disclosure provides a glass composition, a bioactive glass composition, a bioactive dental formulation (e.g., toothpaste), and to methods of making and using the compositions.

In embodiments, the disclosure provides a composition and method for treating dentin hypersensitivity.

In embodiments, the disclosure provides a group of borate and borosilicate bioactive glasses, an oral care product, for example, a toothpaste, a mouthwash, and like formulations, for the treatment of dentin hypersensitivity.

In embodiments, the disclosure provides a glass composition that has a significantly higher rate of occluding of exposed dentin tubules than a 45S5-containing toothpaste, demonstrating excellent properties for treating dentin hypersensitivity.

In embodiments, the present disclosure provides: a bioactive glass composition as defined herein, including or excluding selected source additives.

BRIEF DESCRIPTION OF THE DRAWINGS

In embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed compositions, articles, and methods of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Dentin hypersensitivity," (DH) "dentin sensitivity," (DS) or like terms refer to a short, sharp pain caused by cold and heat, air, touch, or chemical or osmotic stimuli, e.g., sweets.

"Occlude," "occluding," "occlusion," or like terms refer, for example, to close up or block off, to obstruct.

"Glass," "glasses," or like terms can refer to a glass or a glass-ceramic.

"Glass article," or like terms can refer to any object made wholly or partly of glass or a glass-ceramic.

"Flavorant," "flavor" or like terms can refer to any natural or synthetic substance that provides organoleptic properties to the disclosed composition when a user has contact with the composition. The flavorant can be, for example, a single compound or a mixture of compounds. The flavorant can be selected to give the composition or product a unique flavor or to maintain flavor consistency between different product batches or after recipe changes. The flavorant can be any known or discovered compound, for example, diacetyl, acetylpropionyl, acetoin, isoamyl acetate, benzaldehyde, cinnamaldehyde, ethyl propionate, methyl anthranilate, limonene, ethyl decadienoate, allyl hexanoate, ethyl maltol, ethyl vanillin, methyl salicylate, and like compounds, or mixtures thereof.

Other typical composition components or formulation ingredients are known to one of skill in the art such as an abrasive, a humectant, a colorant, an antibacterial agent, a surfactant, a whitening agent, a binder, and like components or ingredients, see for example, en.wikipedia.org/wiki/Toothpaste.

"Angiogenesis ability," "angiogenic," "angiogenesis," or like terms, refer to the physiological process by which new blood vessels form from pre-existing vessels.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Dentin hypersensitivity is a global oral health issue and its treatment remains a significant challenge for most dental professionals. Dentin hypersensitivity is caused by the absence of the smear layer of dentin tubules, which exposes dentinal tubules to thermal, chemical, mechanical, or osmotic stimuli. The movement of the fluid within the tubules stimulates mechanical receptors that are sensitive to fluid pressure, resulting in the transmission of the stimuli to the pulpal nerves and ultimately the pain response. Dentin hypersensitivity can generally be treated, for example, by chemical desensitization of the tooth nerve endings, tubule occluding agents or barriers to reduce dentin permeability, or both (see S. B. Low, "Reduction in dental hypersensitivity with nano-hydroxyapatite, potassium nitrate, sodium monoflurophosphate and antioxidants," Open Dent J, 2015; (9): 92-97; S. Miglani, "Dentin hypersensitivity: Recent trends in management," J Consery Dent. 2010, 13(4): 218-224; A. R. Davari, "Dentin hypersensitivity: Etiology, diagnosis and treatment; a literature review," J Dent (Shiraz), 2013, 14(3): 136-145). The use of potassium nitrate ($KNO_3$) as a chemical desensitization agent can eliminate the potassium ion concentration gradient across the nerve cell membrane. Therefore, the nerve cells will not depolarize and will not respond to stimuli (see S. B. Low, supra.). Current tubule occluding agents include fluorides (i.e., formation of calcium fluoride crystals), oxalates (i.e., formation of calcium oxalate), and strontium chloride (i.e., has affinity for dentine due to the high permeability and possibility for absorption into or onto the organic connective tissues and the odontoblast processes) (see S. Miglani, supra.). Additionally, Pro-Argin-based toothpastes can form a dentin-like mineral deposition layer due to the binding of arginine and calcium carbonate to the negatively charged dentine surface (see R Kulal, "An in-vitro comparison of nano hydroxyapatite, Novamin and Proargin desensitizing toothpastes—a SEM study" J Clin Diagn Res, 2016, 10(10): ZC51-ZC54). Recently, silicate glass based toothpastes such as Novamin® and BioMin® (having for example less than 40% mol $SiO_2$, greater than 8% mol $P_2O_5$), were found to react with saliva and release calcium, phosphate, or in the presence of fluoride ions to form hydroxycarbonated apatite or fluorapatite, respectively, over the exposed dentin and within dentin tubules (see S. Miglani, supra.; L. J. Litkowski, "Compositions containing bioactive glass and their use in treating tooth hypersensitivity," U.S. Pat. No. 6,338,751; and R. Hill, "Bioactive glass composition," U.S. Pat. No. 9,168,272) (see also H. E. Strassler, et al., "Dentinal Hypersensitivity: Etiology, Diagnosis and Management" Contin. Ed. Pub.; and M. Han, et al., "In vivo remineralization of dentin using an agarose hydrogel biomimetic mineralization system," 7 Feb. 2017, in nature.com/srep/).

Dentin treatment using bioactive glass-containing toothpastes is believed to be the only treatment method that can provide long period protection. Unlike other occluding reagents of dentin tubules, a bioactive glass can reliably relieve the pain of dental hypersensitivity for extended periods permanently. Recently developed aluminoborate glasses have been demonstrated to have excellent biocompatability, enhanced angiogenesis, and can promote wound healing, see for example, the abovementioned commonly owned and assigned copending patent applications: 62/342,411 and 62/342,384.

In embodiments, the present disclosure provides an array of borate and borosilicate glass compositions that have superior properties and a capacity to treat dentin hypersensitivity compared to known bioactive glasses.

In embodiments, the present disclosure provides a dental formulation, for example, for oral topical applications, comprising:

a bioactive glass composition in an effective amount, e.g., from 0.1 to 10 wt %, comprising a source of:

2 to 70% $B_2O_3$,
1 to 60% $SiO_2$,
2 to 16% $Al_2O_3$,
5 to 30% CaO,
1 to 6% $P_2O_5$,
1 to 20% $Na_2O$,
1 to 20% $K_2O$, and
1 to 20% MgO, based on a 100 mol % total of the composition; and a suitable carrier, in an effective amount of from 99.9 to 90 wt % based on a 100 wt % total of the composition. The mol % of the source has the equivalent weight percentages of 1 to 60% $B_2O_3$, 1 to 60% $SiO_2$, 2 to 20% $Al_2O_3$, 5 to 25% CaO, 1 to 10% $P_2O_5$, 1 to 20% $Na_2O$, 1 to 25% $K_2O$, and 1 to 15% MgO, based on a 100 wt % total of the composition.

In embodiments, the disclosure provides a bioactive glass comprising a source of from 5 to 50 mol % $SiO_2$ (4 to 40 wt %), and the suitable carrier comprises a source of from 5 to 25 mol % $SiO_2$ (4 to 20 wt %) (e.g., as an abrasive), based on a 100 mol % (100 wt %) total of the composition.

In embodiments, the disclosure provides a dental formulation composition further comprising a source of fluoride ion in an amount of from 1 to 25 mol % (1 to 30 wt %) (see, e.g., U.S. Pat. No. 9,168,272).

In embodiments, the disclosure provides a dental formulation composition wherein the source of fluoride ion is selected, for example, from NaF, $SnF_2$, $CaF_2$, and like sources, or a mixture of selected sources.

In embodiments, the disclosed bioactive glass composition and dental formulation composition containing the disclosed bioactive glass composition can be substantially free-of or entirely free-of a source of fluoride ion.

In embodiments, the disclosed bioactive composition and dental formulation composition containing the disclosed bioactive glass composition can be substantially free-of or entirely free-of a source of titanium oxide.

In embodiments, the disclosure provides a dental formulation composition wherein the bioactive glass composition in an effective amount is from 1 to 20 wt % (e.g., from 1 to 10 wt %) and the suitable carrier in an effective amount is from 80 to 99 wt % (e.g., from 90 to 99 wt %).

In embodiments, the disclosure provides a preferred dental formulation composition wherein the bioactive glass composition comprises:
40 to 60% $B_2O_3$,
0.1 to 5% $SiO_2$,
6 to 10% $Al_2O_3$,
15 to 25% CaO,
1.5 to 2.0% $P_2O_5$,
4 to 8% $Na_2O$,
6 to 10% $K_2O$, and
6 to 10% MgO, based on a 100 mol % total of the composition. The mol % of the source has the equivalent weight percentages of 30 to 50% $B_2O_3$, 0.1 to 5% $SiO_2$, 8 to 15% $Al_2O_3$, 15 to 25% CaO, 1.5 to 5% $P_2O_5$, 4 to 8% $Na_2O$, 6 to 15% $K_2O$, and 3 to 8% MgO, based on a 100 wt % total of the composition.

In embodiments, the disclosure provides a dental formulation composition wherein the suitable carrier comprises one or more ingredients selected from: an abrasive, a humectant, i.e., an anti-drying agent such as glycerol, sorbitol, xylitol, 1,2-propylene glycol, polyethyleneglycol, and like compounds, a flavorant, a colorant, an antibacterial agent, a surfactant, a whitening agent, and other like suitable ingredients known in the art, or a mixture thereof.

In embodiments, the disclosure provides a dental formulation composition wherein the suitable carrier comprises one or more forms selected from: a gum, a paste, a powder, a toothpaste, a mouthwash, a poultice, a tea, a sucker, a spray, and like forms, or a mixture thereof.

In embodiments, the disclosure provides a remineralizing composition comprising: any one of the abovementioned bioactive glass compositions or combinations thereof, and optionally a suitable carrier such as non-aqueous carrier for the remineralizing composition.

In embodiments, the disclosure provides a remineralizing composition comprising: the abovementioned bioactive glass composition and an optional suitable carrier.

In embodiments, the disclosure provides a method of treating dentin hypersensitivity or sensitivity comprising:
contacting a dental surface and any of the abovementioned dental formulations comprising the remineralizing composition.

In embodiments, the contacting the dental formulation has a higher relative rate of from 50 to 95% of occluding exposed dentin tubules compared to a dental formulation base formula that is free-of the bioactive glass, i.e., without the bioactive glass present.

In embodiments, contacting the dental formulation can be selected from at least one of: polishing with a paste formula, rinsing with a liquid formula, injecting with a liquid formula, filling a tooth with a composite, e.g., typically made of powdered bioactive glass and acrylic resin, or a combination thereof.

In embodiments, the dental surface can have at least one of, for example: a dentin surface, a dentin tubule, or a combination thereof.

In embodiments, the disclosure provides a dental formulation comprising:
a bioactive glass composition in an effective amount comprising a source of:
2 to 70% $B_2O_3$,
2 to 16% $Al_2O_3$,
5 to 30% CaO,
1 to 6% $P_2O_5$,
1 to 20% $Na_2O$, and
1 to 20% MgO, based on a 100 mol % total of the composition; and a suitable carrier, in an effective amount based on the combined 100 weight % of the bioactive glass and the carrier. The mol % of the source has the equivalent weight percentages of 1 to 60% $B_2O_3$, 1 to 60% $SiO_2$, 2 to 20% $Al_2O_3$, 5 to 25% CaO, 1 to 10% $P_2O_5$, 1 to 20% $Na_2O$, 1 to 25% $K_2O$, and 1 to 15% MgO, based on a 100 wt % total of the composition.

In embodiments, the dental formulation is free of silica such as a source of $SiO_2$, and free of inorganic potassium salts such as a source of $K_2O$.

In embodiments, the present disclosure is advantaged in several aspects, including for example: the disclosed borate and borosilicate glass compositions can have a significantly higher rate of occluding of the exposed dentin tubules compared to a 45S5-containing toothpaste, which result(s) demonstrate excellent potential of the disclosed bioactive glass for treating dentin hypersensitivity or dentin sensitivity; the disclosed bioactive glass compositions can be free-of inorganic potassium salts, and the disclosed bioactive glass compositions, and dentin treatment formulations, can be silicate free. Novamin® and Biomin® are silicate-containing bioactive glasses.

Figure 3:
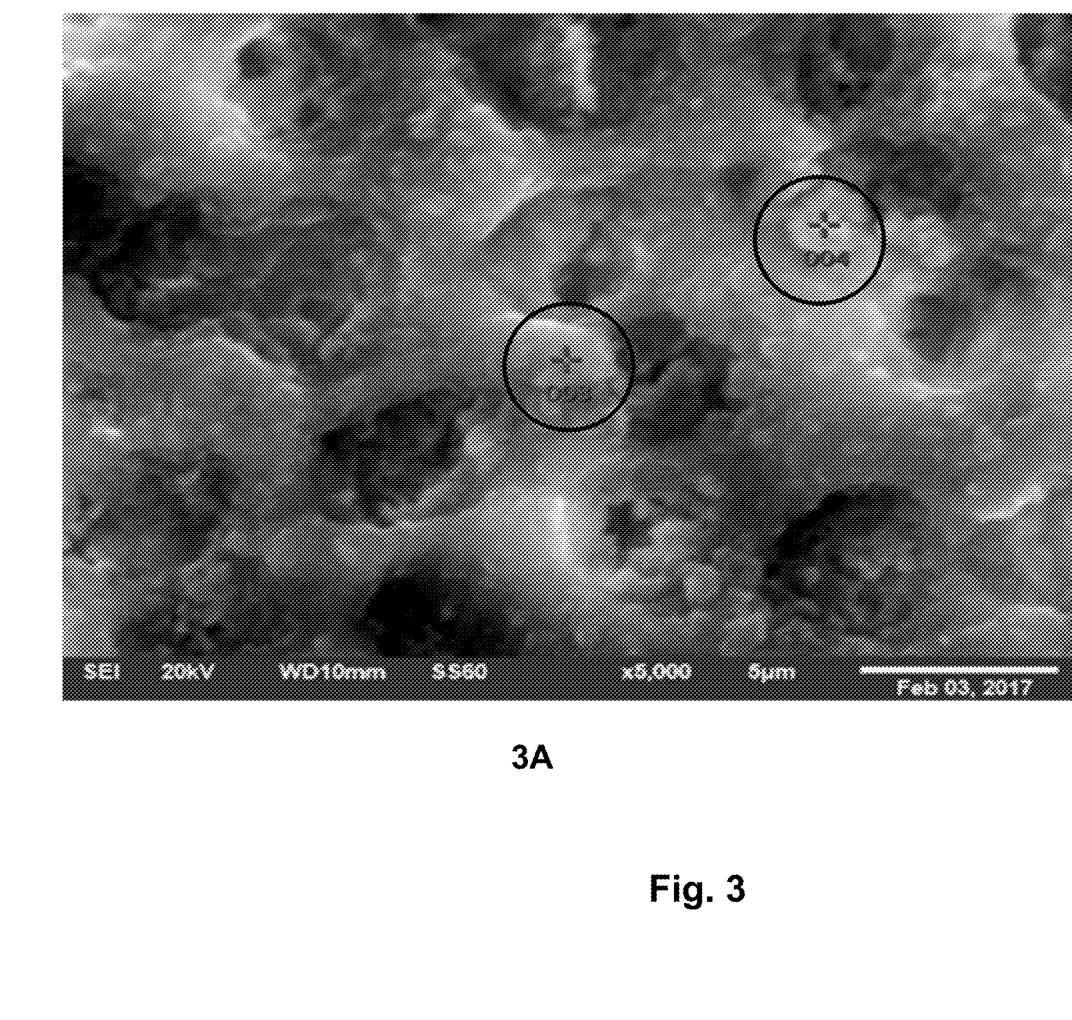
FIGS. 3A to 3C show SEM-EDS analysis of dentin deposition after a 1 week treatment with an Example 1 containing toothpaste formulation.

In embodiments, the disclosure provides borate and borosilicate bioactive glass compositions, for example, as listed in Table 1, that can react with mammalian saliva and can release calcium and phosphate to form hydroxycarbonated apatite, or if fluoride ions are present to form fluorapatite (see FIG. 2 and FIG. 3), exhibiting tubule occlusion at the surface by the formation of a smear layer and within dentin tubules, and rebuild, strengthen, and protect tooth structure. There is also deposition of a trace amount of magnesium in the apatite layer (FIG. 3). Normal enamel and dentin contain, for example, 0.44 and 1.23 wt % of magnesium, respectively. Magnesium is a co-factor for many enzymes, and stabilizes the structures of DNA and RNA. Magnesium may have stimulatory effects on the tooth development and maintenance.

TABLE 1

Bioactive glass compositions in mol percent.

| Glass Example | $SiO_2$ | $B_2O_3$ | $Al_2O_3$ | CaO | $P_2O_5$ | $Na_2O$ | $K_2O$ | MgO |
|---|---|---|---|---|---|---|---|---|
| 1 | 0 | 54.6 | 8 | 22.1 | 1.7 | 6 | 7.9 | 7.7 |
| 2 | 9 | 45 | 8 | 22.1 | 1.7 | 6 | 7.9 | 7.7 |
| 3 | 18 | 36 | 8 | 22.1 | 1.7 | 6 | 7.9 | 7.7 |
| 4 | 27 | 27 | 8 | 22.1 | 1.7 | 6 | 7.9 | 7.7 |
| 5 | 36 | 18 | 8 | 22.1 | 1.7 | 6 | 7.9 | 7.7 |
| 6 | 45 | 9 | 8 | 22.1 | 1.7 | 6 | 7.9 | 7.7 |
| Comparative Ex 7 (45S5 - control) | 46.1 | 0 | 0 | 26.9 | 2.6 | 24.3 | 7.9 | 7.7 |

Fluoride can be incorporated into the glass compositions in a precursor form of, for example, sodium fluoride (NaF), stannous fluoride ($SnF_2$), calcium fluoride ($CaF_2$), and like fluorides or mixtures thereof. The fluoride incorporated glasses can release fluoride and form fluorapatite in an oral fluid. Fluorapatite is more resistant to acid dissolution than hydroxycarbonated apatite.

The fluoride incorporated glasses can also be added into non-aqueous dentifrice matrix, for example, in combination with another bioactive glass. Fluoride ions are known to aid apatite formation and can stimulate osteoblast division.

In addition to their re-mineralizing toothpaste effect, the disclosed glass compositions and formulations can also be antimicrobial, which property permits, for example, prevention of dental caries, reduce plaque formation, control gingivitis, suppress breath malodor, and like beneficial effects. The disclosed glass compositions and formulations can also be incorporated in other professionally applied dental products, such as cleaning and polishing pastes, varnishes, re-mineralizing filling materials, and like formulations.

In embodiments, the disclosure provides a remineralizing composition comprising, for example:
a bioactive glass composition in an effective amount, e.g., from 0.1 to 10 wt %, comprising a source of:
2 to 70% $B_2O_3$,
1 to 60% $SiO_2$,
2 to 16% $Al_2O_3$,
5 to 30% CaO,
1 to 6% $P_2O_5$,
1 to 20% $Na_2O$,
1 to 20% $K_2O$, and
1 to 20% MgO, based on a 100 mol % total of the composition, and optionally further comprising a suitable carrier in from 80 to 99.9 wt % to the bioactive glass in from 0.1 to 20 wt % based on the total weight of the composition and carrier. The mol % of the source has the equivalent weight percentages of 1 to 60% $B_2O_3$, 1 to 60% $SiO_2$, 2 to 20% $Al_2O_3$, 5 to 25% CaO, 1 to 10% $P_2O_5$, 1 to 20% $Na_2O$, 1 to 25% $K_2O$, and 1 to 15% MgO, based on a 100 wt % total of the composition.

Figure 1:
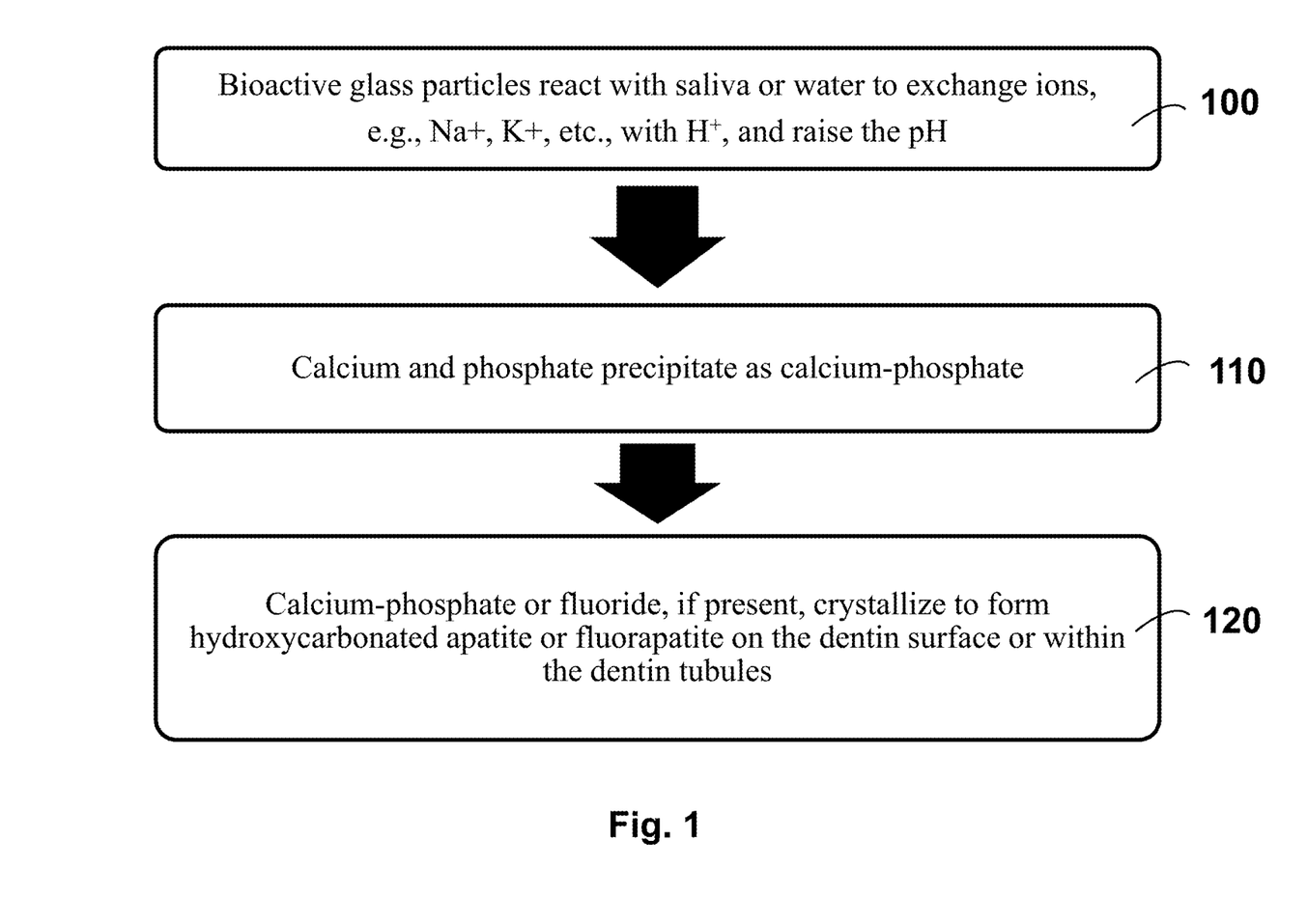
FIG. 1 shows a hypothetical scheme of chemical and physical action of the disclosed bioactive composition.
Figure 2:
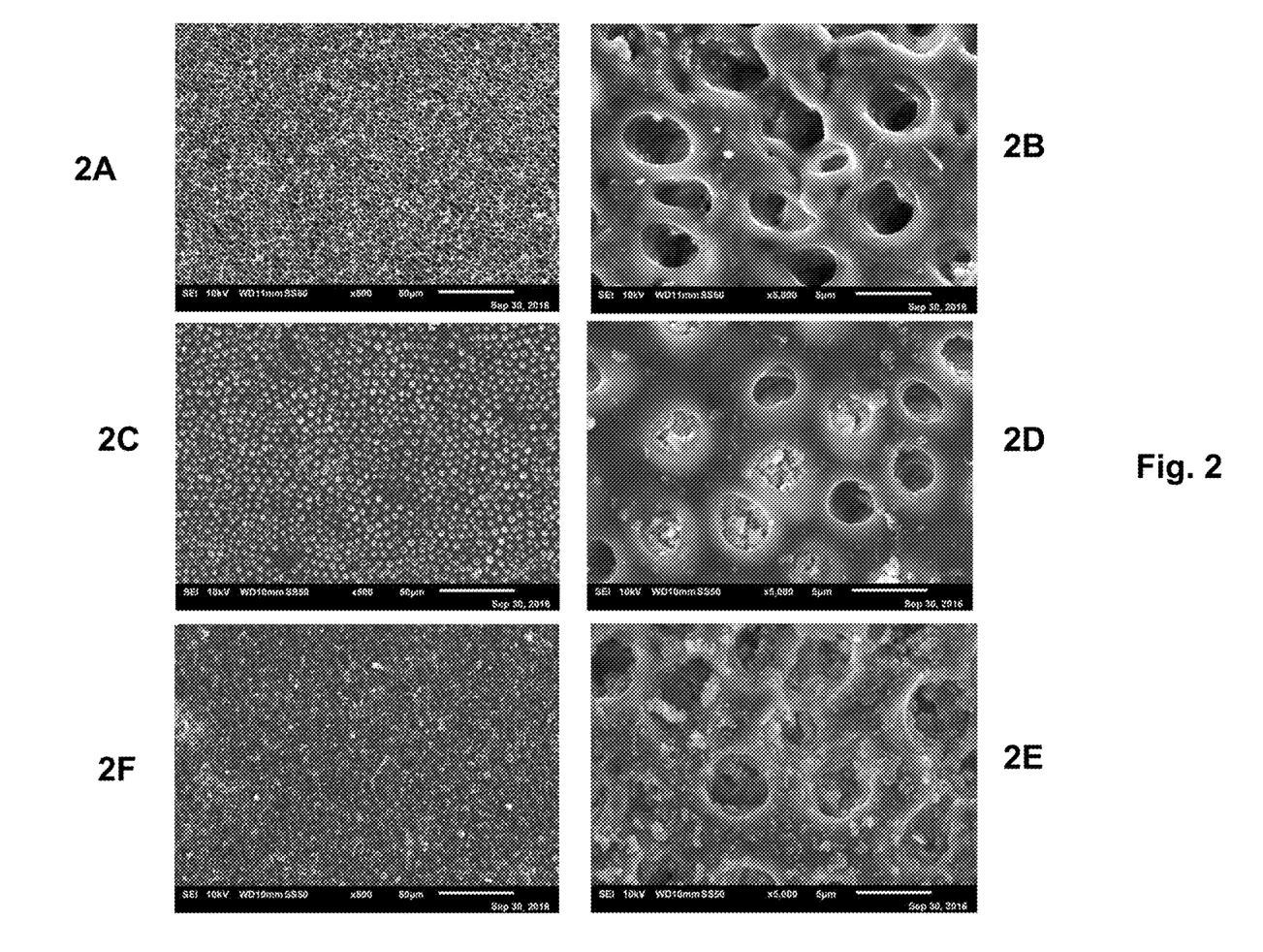
FIGS. 2A to 2F show SEM micrographs of test dentin discs after 1 week treatment with various formulations.

Referring to the Figures, FIG. 1 shows a hypothetical scheme of chemical and physical action of the disclosed bioactive composition. The mechanism of action, although not limited by theory, is believed to include, for example: the bioactive glass particles react with saliva or water to exchange ions, e.g., $Na^+$, $K^+$, and like ions, with $H^+$, and raise the pH (100); calcium and phosphate precipitate as calcium-phosphate (110); and calcium-phosphate, or fluoride if present, crystallize to form hydroxycarbonated apatite or fluorapatite on the dentin surface or within the dentin tubules (120).

FIGS. 2A to 2F show SEM micrographs of test dentin discs after 1 week treatment: with a base toothpaste formulation (2A, 2B); a 45S5-containing toothpaste (2C, 2D); or an Example 1 containing toothpaste (2E, 2F), and immersion in artificial saliva. There was no occluding of dentin tubules for the base toothpaste treatment. After treatment with the 45S5 containing toothpaste, dentin tubules were partially occluded by crystal-like deposits. After treatment with the Example 1 containing toothpaste, most dentin tubules and dentin surface were occluded by crystal-like deposits.

FIGS. 3A to 3C show SEM-EDS analysis of dentin deposition after a 1 week treatment with the Example 1 containing toothpaste. FIG. 3A shows the SEM having two points selected (black circles added) for further analysis. SEM-EDS analysis showed the apatite formed on and within the dentin tubules were calcium and phosphate precipitate and small trace of magnesium (see FIGS. 3B (point 003) and 3C (point 004)).

Materials and Methods

Each glass composition of Table 1 was separately melted and ground to 1 to 10 microns using, for example, an air jet mill.

Each ground glass composition of Table 1 was separately formulated into a dental formulation such as listed in Table 2.

Each dental formulation was evaluated for the ability to occlude dentine discs made of human molars as detailed in Example 9, i.e., the discs having dentin tubules were exposed to the dental formulation and compared to a dental formulation base (control) that was free-of the disclosed bioactive glass.

TABLE 2

Base and an exemplary BG* containing toothpaste composition.

| Ingredients | Base (control) | Toothpaste (base + BG*) |
|---|---|---|
| glycerol | 69.02 | 64.02 |
| sodium lauryl sulphate | 1.1 | 1.1 |
| PEG400 | 20 | 20 |
| silicon dioxide | 8 | 8 |
| *bioactive glass (BG) | — | 5 |
| carbopol 940 | 0.5 | 0.5 |
| sodium saccharin | 0.35 | 0.35 |
| flavor | 1.03 | 1.03 |
| Total (wt %) | 100 | 100 |

Raw materials, equipment, or both, used to produce the compositions of the present disclosure, can introduce certain impurities or components that are not intentionally added, and can be present in the final glass composition. Such materials can be present in the disclosed compositions in minor amounts and are referred to as "tramp materials."

Disclosed compositions can comprise the tramp materials, typically in trace amounts. Similarly, "iron-free," "sodium-free," "lithium-free," "zirconium-free," "alkali earth metal-free," "heavy metal-free," or like descriptions, mean that the tramp material was not purposefully added to the composition, but the composition may still comprise iron, sodium, lithium, zirconium, alkali earth metals, or heavy metals, etc., but in approximately tramp or trace amounts.

Unless otherwise specified, the concentrations of all constituents recited herein are expressed in terms of weight percent (wt %).

EXAMPLES

The following Examples demonstrate making, use, and analysis of the disclosed compositions, formulations, and methods in accordance with the above general procedures.

Example 1

Glass 1 The composition of Example 1 in Table 1 was prepared as follows: The source batch materials in the indicated amounts, including silicon dioxide, boric acid, alumina, sodium oxide, potassium oxide, limestone, magnesium oxide, and calcium phosphate, were individually combined. The batch source materials were vigorously mixed in a plastic jar using a Turbular mixer. Then they were transferred to a platinum crucible with an internal volume of approximately 650 cc. The crucible was then loaded into an annealing furnace to calcine the batch at 250° C. for 24 hr. The calcined batches were then melted at 1100 to 1300° C. for 6 hr and then the glass melt was poured on a steel plate, and annealed at 400 to 500° C.

Examples 2 to 6

Glasses 2 through 6 were likewise prepared as in Example 1 with the exception that the composition or amount used in the batch was different and as listed in Table 1.

Comparative Example 7

Comparative Glass 7 The composition of Comparative Example 7 in Table 1 was prepared as in Example 1 with the exception that: there is no boric acid or alumina batched in the comparative glass, see for example US 20140186274, which mentions a non-aqueous base composition in combination with a bioactive glass.

Example 8

Dental Formulation The dental formulations of Table 2 were prepared as follows: Glycerol and PEG 400 were added to the glass composition first, then the remaining ingredients of the formulation were separately added and thoroughly mixed with a spatula.

Example 9

Evaluation of Dental Formulation The dental formulations of Table 2 were evaluated as follows: Human molars were lawfully obtained from bforbones (bforbones.com). Dentine discs having a thickness of 1 mm were cut perpendicularly to the long axis of the tooth above the cemento-enamel junction using a Buehler low-speed water cooled diamond saw. A smear layer was created on both sides of the dentine discs by sanding 30 seconds using 500-grit sanding paper. The smear was subsequently removed by treating with 6% citric acid for 3 mins, then rinsed with water, and dried at 37° C. The dentine discs were randomly divided into control or experiment groups, each containing at least 3 specimens, which received either a non-aqueous toothpaste base formulation or a toothpaste containing 5% of 45S5; and the toothpaste containing a disclosed glass composition, as listed in Tables 1 and 2. The toothpaste and a powered tooth brush were used to brush against both sides of the dentin discs for 1 min per side. The specimens were then rinsed with distilled water to remove visible traces of toothpaste, and then stored in artificial saliva (1.5 mM $CaCl_2$, 0.9 mM $KH_2PO_4$, 130 mM KCl, and 20 mM HEPES with pH 7.4). The procedure of brushing, rinsing, and storing each specimen in artificial saliva was repeated twice a day for 7 days, then the specimens were dried at 37° C. for 16 hrs and stored at RT before SEM.

The disclosure has been described with reference to various specific embodiments and techniques. However, many variations and modifications are possible while remaining within the scope of the disclosure.

What is claimed is:

1. A dental formulation comprising:
    an effective amount of a bioactive glass composition consisting of:
        40 to 60% $B_2O_3$,
        0 to 5% $SiO_2$,
        6 to 10% $Al_2O_3$,
        15 to 25% CaO,
        1.5 to 2% $P_2O_5$,
        4 to 8% $Na_2O$,
        6 to 10% $K_2O$, and
        6 to 10% MgO, based on a 100 mol % total of the bioactive glass composition; and
    an effective amount of a suitable carrier, based on the combined weight of the bioactive glass composition and the carrier.

2. The dental formulation of claim 1 wherein the suitable carrier comprises a source of silica of from 1 to 25 wt % $SiO_2$ by addition to the bioactive glass composition.

3. The dental formulation of claim 1 wherein the effective amount of the bioactive glass composition is from 0.1 to 10 wt %, and the effective amount of the suitable carrier is from 90 to 99.9 wt %.

4. The dental formulation of claim 1 wherein the suitable carrier comprises one or more ingredients selected from: an abrasive, a humectant, a flavorant, a colorant, an antibacterial agent, a surfactant, a whitening agent, a binder, or a mixture thereof.

5. The dental formulation of claim 1 wherein the suitable carrier comprises one or more forms selected from: a gum, a paste, a powder, a toothpaste, a mouthwash, a poultice, a tea, a sucker, or a spray.

6. The dental formulation of claim 1 wherein the formulation is a remineralizing composition.

7. The remineralizing composition of claim 6 wherein the effective amount of the suitable carrier is from 80 to 99.9 wt % and the effective amount of the bioactive glass composition is from 0.1 to 20 wt % based on the total weight of the bioactive glass composition and carrier.

8. A method of treating dentin hypersensitivity comprising:
    contacting the dental formulation of claim 1 to a dental surface.

9. The method of claim 8, wherein contacting the dental formulation has a higher rate of from 50 to 95% of occluding exposed dentin tubules compared to a dental formulation base that is free-of the bioactive glass.

10. The method of claim 8, wherein the dental formulation is selected from: a polish comprising a paste formula, a rinse comprising a liquid formula, an injectable comprising a liquid formula, a tooth filling comprising a composite, or a combination thereof.

11. The method of claim 8, wherein the dental surface has: a dentin surface, a dentin tubule, or a combination thereof.

* * * * *

UNITED STATES PATENT AND TRADEMARK OFFICE
CERTIFICATE OF CORRECTION

PATENT NO. : 11,274,059 B2
APPLICATION NO. : 16/203002
DATED : March 15, 2022
INVENTOR(S) : Huayun Deng et al.

It is certified that error appears in the above-identified patent and that said Letters Patent is hereby corrected as shown below:

On the Title Page

On the page 2, in Column 2, Item (56) under "Other Publications", Line 1, delete "Additiona" and insert -- Additional --.

On the page 2, in Column 2, Item (56) under "Other Publications", Line 2, delete "Phosphate-Baed" and insert -- Phosphate-Based --.

On the page 2, in Column 2, Item (56) under "Other Publications", Line 4, delete "902472;" and insert -- 902427; --.

On the page 3, in Column 1, Item (56) under "Other Publications", Line 18, delete "SiO2Na20." and insert -- SiO2Na2O. --.

On the page 3, in Column 1, Item (56) under "Other Publications", Line 64, delete "Microplasitcs" and insert -- Microplastics --.

On the page 3, in Column 2, Item (56) under "Other Publications", Line 72, delete "Propmotes" and insert -- Promotes --.

On the page 4, in Column 1, Item (56) under "Other Publications", Line 9, delete "Properites" and insert -- Properties --.

On the page 4, in Column 1, Item (56) under "Other Publications", Line 18, delete "stronium-doped" and insert -- strontium-doped --.

On the page 4, in Column 1, Item (56) under "Other Publications", Line 28, delete "Rahman" and insert -- Rahaman --.

Signed and Sealed this
Fourth Day of October, 2022

Katherine Kelly Vidal
*Director of the United States Patent and Trademark Office*

CERTIFICATE OF CORRECTION (continued)
U.S. Pat. No. 11,274,059 B2

On the page 4, in Column 1, Item (56) under "Other Publications", Lines 46-47, delete "Si02-Na20-Fe203-Ca0-P205_B203" and insert -- SiO2-Na2O-Fe2O3-CaO-P2O5_B2O3 --.

On the page 4, in Column 1, Item (56) under "Other Publications", Line 50, delete "www.indeedce.com." and insert -- www.indeed.com. --.

On the page 4, in Column 2, Item (56) under "Other Publications", Line 6, delete "P205" and insert -- P2O5 --.

On the page 4, in Column 2, Item (56) under "Other Publications", Line 30, delete "Al2O" and insert -- Al2O3 --.

On the page 4, in Column 2, Item (56) under "Other Publications", Line 36, delete "aspromising" and insert -- as promising --.

On the page 4, in Column 2, Item (56) under "Other Publications", Line 44, delete "aqueuous" and insert -- aqueous --.

On the page 4, in Column 2, Item (56) under "Other Publications", Line 45, delete "2006," and insert -- 2008, --.

On the page 4, in Column 2, Item (56) under "Other Publications", Line 51, delete "2010." and insert -- 2010). --.